(12) United States Patent
Nelson et al.

(10) Patent No.: US 8,434,487 B2
(45) Date of Patent: *May 7, 2013

(54) ENDOTRACHEAL CUFF AND TECHNIQUE FOR USING THE SAME

(75) Inventors: Donald S. Nelson, San Ramon, CA (US); Dhairya Mehta, Skokie, IL (US)

(73) Assignee: Covidien LP, Mansfield, MA (US)

( * ) Notice: Subject to any disclaimer, the term of this patent is extended or adjusted under 35 U.S.C. 154(b) by 798 days.

This patent is subject to a terminal disclaimer.

(21) Appl. No.: 11/472,733

(22) Filed: Jun. 22, 2006

(65) Prior Publication Data

US 2007/0295336 A1    Dec. 27, 2007

(51) Int. Cl.
*A61M 11/00* (2006.01)
(52) U.S. Cl.
USPC .................................................. 128/207.15
(58) Field of Classification Search ........ 128/207.14–207.18, 207.29
See application file for complete search history.

(56) References Cited

U.S. PATENT DOCUMENTS

| | | | |
|---|---|---|---|
| 2,099,127 A | 11/1937 | Leech | |
| 2,133,345 A | 10/1938 | Davis | |
| 2,765,559 A | 10/1956 | Morris | |
| 2,927,584 A | 3/1960 | Wallace | |
| 3,709,227 A | 1/1973 | Hayward | |
| 3,734,100 A | 5/1973 | Walker et al. | |
| 3,769,983 A | 11/1973 | Merav | |
| 3,810,474 A | 5/1974 | Cross | |
| 3,822,238 A | 7/1974 | Blair et al. | |
| 3,913,565 A | 10/1975 | Kawahara | |
| 3,971,385 A | 7/1976 | Corbett | |
| 3,975,350 A | 8/1976 | Hudgin et al. | |
| 3,995,643 A | 12/1976 | Merav | |
| 4,022,217 A | 5/1977 | Rowean | |
| 4,130,617 A | 12/1978 | Wallace | |
| 4,230,108 A | 10/1980 | Young | |
| 4,231,365 A | 11/1980 | Scarberry | |
| 4,235,239 A | 11/1980 | Elam | |
| 4,340,046 A | 7/1982 | Cox | |
| 4,511,354 A * | 4/1985 | Sterling | 604/98.01 |
| 4,569,344 A | 2/1986 | Palmer | |
| 4,638,539 A | 1/1987 | Palmer | |
| 4,649,913 A | 3/1987 | Watson | |
| 4,696,296 A | 9/1987 | Palmer | |
| 4,700,700 A | 10/1987 | Eliachar | |
| 4,791,920 A | 12/1988 | Fauza | |
| 4,825,859 A | 5/1989 | Lambert | |
| 4,825,861 A | 5/1989 | Koss | |

(Continued)

FOREIGN PATENT DOCUMENTS

| CA | 2353007 A1 | 6/2000 |
|---|---|---|
| CA | 20072654938 | 6/2007 |

(Continued)

OTHER PUBLICATIONS

Tecogel brochure page, Noveon Thermedics Polymer Products, Oct. 2003.

(Continued)

*Primary Examiner* — Steven Douglas (57) ABSTRACT

An inflatable balloon cuff may be adapted to seal a patient's trachea when associated with an endotracheal tube. Configurations of these cuffs that include tapered regions with certain characteristics, such as cuff wall diameter and thickness, may provide improved sealing of the trachea.

46 Claims, 8 Drawing Sheets

U.S. PATENT DOCUMENTS

| | | | |
|---|---|---|---|
| 4,834,726 A | 5/1989 | Lambert | |
| 4,836,199 A | 6/1989 | Palmer | |
| 4,838,255 A | 6/1989 | Lambert | |
| 4,850,348 A | 7/1989 | Pell et al. | |
| 4,867,153 A | 9/1989 | Lorenzen et al. | |
| 4,872,579 A | 10/1989 | Palmer | |
| 4,886,059 A | 12/1989 | Weber | |
| 4,927,412 A | 5/1990 | Menasche | |
| 4,938,741 A | 7/1990 | Lambert | |
| 4,963,313 A | 10/1990 | Noddin et al. | |
| 4,967,743 A | 11/1990 | Lambert | |
| 4,979,505 A | 12/1990 | Cox | |
| 5,020,534 A | 6/1991 | Pell et al. | |
| 5,021,045 A | 6/1991 | Buckberg et al. | |
| 5,025,806 A | 6/1991 | Palmer et al. | |
| 5,029,580 A | 7/1991 | Radford et al. | |
| 5,033,466 A | 7/1991 | Weymuller, Jr. | |
| 5,060,646 A | 10/1991 | Page | |
| 5,065,754 A | 11/1991 | Jensen | |
| 5,074,840 A | 12/1991 | Yoon | |
| 5,076,268 A | 12/1991 | Weber | |
| 5,098,379 A | 3/1992 | Conway et al. | |
| 5,103,816 A | 4/1992 | Krischbaum et al. | |
| 5,107,829 A | 4/1992 | Lambert | |
| 5,120,322 A | 6/1992 | Davis et al. | |
| 5,122,122 A | 6/1992 | Allgood | |
| 5,133,345 A | 7/1992 | Lambert | |
| 5,135,516 A | 8/1992 | Sahatjian et al. | |
| 5,137,671 A | 8/1992 | Conway et al. | |
| 5,158,569 A | 10/1992 | Strickland et al. | |
| 5,165,420 A | 11/1992 | Strickland | |
| 5,176,638 A | 1/1993 | Don Michael | |
| 5,190,810 A | 3/1993 | Kirschbaum et al. | |
| 5,199,427 A | 4/1993 | Strickland | |
| 5,201,310 A | 4/1993 | Turnbull et al. | |
| 5,207,643 A | 5/1993 | Davis | |
| 5,215,522 A | 6/1993 | Page et al. | |
| 5,218,957 A | 6/1993 | Strickland | |
| 5,230,332 A | 7/1993 | Strickland | |
| 5,233,979 A | 8/1993 | Strickland | |
| 5,246,012 A | 9/1993 | Strickland | |
| 5,250,070 A | 10/1993 | Parodi | |
| 5,251,619 A | 10/1993 | Lee | |
| 5,261,896 A | 11/1993 | Conway et al. | |
| 5,263,478 A | 11/1993 | Davis | |
| 5,269,770 A | 12/1993 | Conway et al. | |
| 5,277,177 A | 1/1994 | Page et al. | |
| 5,285,777 A | 2/1994 | Beckwith | |
| 5,290,585 A | 3/1994 | Elton | |
| 5,304,121 A | 4/1994 | Sahatjian | |
| 5,305,740 A | 4/1994 | Kolobow | |
| 5,331,027 A | 7/1994 | Whitbourne | |
| 5,360,402 A | 11/1994 | Conway et al. | |
| 5,370,656 A | 12/1994 | Shevel | |
| 5,370,899 A | 12/1994 | Conway et al. | |
| 5,374,261 A | 12/1994 | Yoon | |
| 5,392,787 A | 2/1995 | Yoon | |
| 5,397,302 A | 3/1995 | Weaver et al. | |
| 5,407,423 A | 4/1995 | Yoon | |
| 5,417,671 A | 5/1995 | Jackson | |
| 5,423,745 A | 6/1995 | Todd et al. | |
| 5,423,754 A | 6/1995 | Cornelius et al. | |
| 5,439,457 A | 8/1995 | Yoon | |
| 5,443,063 A | 8/1995 | Greenberg | |
| 5,447,152 A * | 9/1995 | Kohsai et al. | 128/207.15 |
| 5,447,505 A | 9/1995 | Valentine et al. | |
| 5,451,204 A | 9/1995 | Yoon | |
| 5,466,231 A | 11/1995 | Cercone et al. | |
| 5,469,864 A | 11/1995 | Rosenblatt | |
| 5,482,740 A | 1/1996 | Conway et al. | |
| 5,484,426 A | 1/1996 | Yoon | |
| 5,487,730 A | 1/1996 | Marcadis et al. | |
| 5,494,029 A | 2/1996 | Lane et al. | |
| 5,501,669 A | 3/1996 | Conway et al. | |
| 5,507,284 A | 4/1996 | Daneshvar | |
| 5,509,899 A | 4/1996 | Fan et al. | |
| 5,524,642 A | 6/1996 | Rosenblatt | |
| 5,545,132 A | 8/1996 | Fagan et al. | |
| 5,556,391 A | 9/1996 | Cercone et al. | |
| 5,567,203 A | 10/1996 | Euteneuer et al. | |
| 5,593,718 A | 1/1997 | Conway et al. | |
| 5,599,292 A | 2/1997 | Yoon | |
| 5,599,299 A | 2/1997 | Weaver et al. | |
| 5,599,321 A | 2/1997 | Conway et al. | |
| 5,611,336 A | 3/1997 | Page et al. | |
| 5,613,950 A | 3/1997 | Yoon | |
| 5,620,457 A * | 4/1997 | Pinchasik et al. | 606/194 |
| 5,649,902 A | 7/1997 | Yoon | |
| 5,653,229 A | 8/1997 | Greenberg | |
| 5,670,111 A | 9/1997 | Conway et al. | |
| 5,674,192 A | 10/1997 | Sahatjian et al. | |
| 5,693,014 A | 12/1997 | Abele et al. | |
| 5,694,902 A | 12/1997 | Miwa et al. | |
| 5,694,922 A | 12/1997 | Palmer | |
| 5,697,365 A | 12/1997 | Pell | |
| 5,700,239 A | 12/1997 | Yoon | |
| 5,715,815 A | 2/1998 | Lorenzen et al. | |
| 5,720,726 A | 2/1998 | Marcadis et al. | |
| 5,722,931 A | 3/1998 | Heaven | |
| 5,730,123 A | 3/1998 | Lorenzen | |
| 5,733,252 A | 3/1998 | Yoon | |
| 5,735,271 A | 4/1998 | Lorenzen et al. | |
| 5,746,762 A | 5/1998 | Bass | |
| 5,765,559 A | 6/1998 | Kim | |
| 5,769,882 A | 6/1998 | Fogarty et al. | |
| 5,810,786 A | 9/1998 | Jackson et al. | |
| 5,819,733 A | 10/1998 | Bertram | |
| 5,827,215 A | 10/1998 | Yoon | |
| 5,843,017 A | 12/1998 | Yoon | |
| 5,843,028 A | 12/1998 | Weaver et al. | |
| 5,843,060 A | 12/1998 | Cercone | |
| 5,843,089 A | 12/1998 | Sahatjian et al. | |
| 5,868,719 A | 2/1999 | Tsukernik | |
| 5,868,775 A | 2/1999 | Bircoll | |
| 5,908,406 A | 6/1999 | Ostapchenko | |
| 5,951,597 A | 9/1999 | Westlund et al. | |
| 5,954,706 A | 9/1999 | Sahatjian | |
| 5,954,740 A | 9/1999 | Ravenscroft et al. | |
| 5,970,111 A | 10/1999 | Samarasekera et al. | |
| 5,971,954 A | 10/1999 | Conway et al. | |
| 5,974,192 A | 10/1999 | Kundu | |
| 5,976,072 A | 11/1999 | Greenberg | |
| 5,976,199 A | 11/1999 | Wu et al. | |
| 5,997,503 A | 12/1999 | Willis et al. | |
| 5,997,546 A | 12/1999 | Foster et al. | |
| 6,010,480 A | 1/2000 | Abele et al. | |
| 6,012,451 A | 1/2000 | Palmer | |
| 6,048,332 A | 4/2000 | Duffy et al. | |
| 6,110,192 A | 8/2000 | Ravenscroft et al. | |
| 6,123,698 A | 9/2000 | Spears et al. | |
| 6,129,547 A | 10/2000 | Cise | |
| 6,143,318 A | 11/2000 | Gilchrist et al. | |
| 6,152,136 A | 11/2000 | Pagan | |
| 6,169,123 B1 | 1/2001 | Cercone | |
| 6,210,364 B1 | 4/2001 | Anderson et al. | |
| 6,214,895 B1 | 4/2001 | Cercone | |
| 6,227,200 B1 | 5/2001 | Crump et al. | |
| 6,240,321 B1 | 5/2001 | Janke et al. | |
| 6,248,088 B1 | 6/2001 | Yoon | |
| 6,264,631 B1 | 7/2001 | Willis et al. | |
| 6,264,633 B1 | 7/2001 | Knorig | |
| 6,277,089 B1 | 8/2001 | Yoon | |
| 6,312,421 B1 | 11/2001 | Boock | |
| 6,322,586 B1 | 11/2001 | Monroe et al. | |
| 6,364,856 B1 | 4/2002 | Ding et al. | |
| 6,378,521 B1 | 4/2002 | Van Den Berg | |
| 6,394,093 B1 | 5/2002 | Lethi | |
| 6,395,012 B1 | 5/2002 | Yoon et al. | |
| 6,398,266 B1 | 6/2002 | Crump | |
| 6,409,716 B1 | 6/2002 | Sahatjian et al. | |
| 6,481,436 B1 | 11/2002 | Neame | |
| 6,494,203 B1 | 12/2002 | Palmer | |
| 6,524,274 B1 | 2/2003 | Rosenthal et al. | |
| 6,526,977 B1 | 3/2003 | Göbel | |
| 6,528,150 B2 | 3/2003 | Nazarova et al. | |
| 6,543,451 B1 | 4/2003 | Crump et al. | |
| 6,551,272 B2 | 4/2003 | Göbel | |

| | | | |
|---|---|---|---|
| 6,572,813 B1 | 6/2003 | Zhang et al. | |
| 6,584,970 B1 | 7/2003 | Crump et al. | |
| 6,588,425 B2 | 7/2003 | Rouns et al. | |
| 6,588,427 B1 | 7/2003 | Carlsen et al. | |
| 6,602,218 B2 | 8/2003 | Yoon | |
| 6,602,219 B2 | 8/2003 | Madsen et al. | |
| 6,607,545 B2 | 8/2003 | Kammerer et al. | |
| 6,609,520 B1 | 8/2003 | Carlsen et al. | |
| 6,612,304 B1 | 9/2003 | Cise et al. | |
| 6,612,305 B2 | 9/2003 | Fauza | |
| 6,613,025 B1 | 9/2003 | Palasis | |
| 6,615,835 B1 | 9/2003 | Cise et al. | |
| 6,619,530 B2 | 9/2003 | Ushiki et al. | |
| 6,620,128 B1 | 9/2003 | Simhambhatla | |
| 6,623,450 B1 | 9/2003 | Dutta | |
| 6,629,530 B1 | 10/2003 | Cise | |
| 6,632,091 B1 | 10/2003 | Cise et al. | |
| 6,638,245 B2 | 10/2003 | Miller et al. | |
| 6,651,664 B1 | 11/2003 | Lomholt | |
| 6,688,306 B1 | 2/2004 | Cise et al. | |
| 6,698,424 B2 | 3/2004 | Madsen et al. | |
| 6,705,320 B1 | 3/2004 | Anderson | |
| 6,712,832 B2 * | 3/2004 | Shah | 606/192 |
| 6,722,368 B1 | 4/2004 | Shaikh | |
| 6,726,696 B1 | 4/2004 | Houser et al. | |
| 6,745,773 B1 | 6/2004 | Gobel | |
| 6,746,424 B2 | 6/2004 | Stamberg | |
| 6,767,340 B2 | 7/2004 | Willis et al. | |
| 6,767,640 B2 | 7/2004 | Moffatt | |
| 6,769,430 B1 | 8/2004 | Carlsen et al. | |
| 6,770,066 B1 | 8/2004 | Weaver et al. | |
| 6,772,368 B2 | 8/2004 | Dhong et al. | |
| 6,786,876 B2 | 9/2004 | Cox | |
| 6,790,221 B2 | 9/2004 | Monroe et al. | |
| 6,796,309 B2 | 9/2004 | Nash et al. | |
| 6,802,317 B2 | 10/2004 | Göbel | |
| 6,805,125 B1 | 10/2004 | Crump et al. | |
| 6,808,521 B1 | 10/2004 | McMichael | |
| 6,814,730 B2 | 11/2004 | Li | |
| 6,890,339 B2 | 5/2005 | Sahatjian et al. | |
| 6,908,449 B2 | 6/2005 | Willis et al. | |
| 6,916,307 B2 | 7/2005 | Willis et al. | |
| 6,923,786 B2 | 8/2005 | Rouns et al. | |
| 6,997,909 B2 | 2/2006 | Goldberg | |
| 7,040,321 B2 | 5/2006 | Gobel | |
| 7,040,322 B2 | 5/2006 | Fortuna et al. | |
| 7,066,905 B2 | 6/2006 | Squire et al. | |
| 7,147,252 B2 | 12/2006 | Teuscher et al. | |
| 7,258,120 B2 | 8/2007 | Melker | |
| 2001/0016724 A1 | 8/2001 | Davis et al. | |
| 2002/0032407 A1 | 3/2002 | Willis et al. | |
| 2002/0077603 A1 | 6/2002 | Willis et al. | |
| 2002/0077604 A1 | 6/2002 | Willis et al. | |
| 2002/0078960 A1 | 6/2002 | Cise | |
| 2002/0078963 A1 | 6/2002 | Rouns et al. | |
| 2002/0082552 A1 | 6/2002 | Ding et al. | |
| 2002/0082553 A1 | 6/2002 | Duchamp | |
| 2002/0091375 A1 | 7/2002 | Sahatjian et al. | |
| 2002/0193753 A1 | 12/2002 | Rouns et al. | |
| 2002/0195110 A1 | 12/2002 | Watton | |
| 2003/0000526 A1 | 1/2003 | Gobel | |
| 2003/0069620 A1 | 4/2003 | Li | |
| 2003/0111077 A1 | 6/2003 | Hooser et al. | |
| 2003/0116162 A1 | 6/2003 | Madsen et al. | |
| 2003/0116963 A1 | 6/2003 | Teuscher et al. | |
| 2003/0225369 A1 | 12/2003 | McMichael et al. | |
| 2003/0225392 A1 | 12/2003 | McMichael et al. | |
| 2003/0225393 A1 | 12/2003 | McMichael et al. | |
| 2004/0024363 A1 | 2/2004 | Goldberg | |
| 2004/0079376 A1 | 4/2004 | Melker | |
| 2004/0092870 A1 | 5/2004 | Squire et al. | |
| 2004/0106899 A1 | 6/2004 | McMichael et al. | |
| 2004/0106900 A1 | 6/2004 | Triebes et al. | |
| 2004/0106901 A1 | 6/2004 | Letson et al. | |
| 2004/0116898 A1 | 6/2004 | Hawk | |
| 2004/0152945 A1 | 8/2004 | Kantrowitz et al. | |
| 2004/0154623 A1 | 8/2004 | Schaeffer | |
| 2004/0193100 A1 | 9/2004 | Van Hooser et al. | |
| 2004/0193101 A1 | 9/2004 | Van Hooser et al. | |
| 2004/0215142 A1 | 10/2004 | Matheis et al. | |
| 2004/0220534 A1 * | 11/2004 | Martens et al. | 604/265 |
| 2004/0221853 A1 | 11/2004 | Miller | |
| 2004/0255951 A1 | 12/2004 | Grey | |
| 2004/0255952 A1 | 12/2004 | Carlsen et al. | |
| 2005/0004560 A1 | 1/2005 | Cox | |
| 2005/0033267 A1 | 2/2005 | Decaria | |
| 2005/0033268 A1 | 2/2005 | Decaria | |
| 2005/0033269 A1 | 2/2005 | Decaria | |
| 2005/0038381 A1 | 2/2005 | McMichael | |
| 2005/0065468 A1 | 3/2005 | Goebel | |
| 2005/0124932 A1 | 6/2005 | Foster et al. | |
| 2005/0124935 A1 | 6/2005 | McMichael | |
| 2005/0137619 A1 | 6/2005 | Schewe et al. | |
| 2005/0166924 A1 | 8/2005 | Thomas et al. | |
| 2007/0038109 A1 | 2/2007 | Nierich | |
| 2007/0295336 A1 | 12/2007 | Nelson et al. | |
| 2007/0295337 A1 | 12/2007 | Nelson | |
| 2007/0296125 A1 | 12/2007 | Colburn et al. | |
| 2008/0000482 A1 | 1/2008 | Maguire et al. | |
| 2008/0210243 A1 | 9/2008 | Clayton et al. | |
| 2008/0236593 A1 | 10/2008 | Nelson et al. | |
| 2013/0000650 A1 | 1/2013 | Nelson | |
| 2013/0008451 A1 | 1/2013 | Nelson | |

FOREIGN PATENT DOCUMENTS

| | | |
|---|---|---|
| CA | 2654938 | 12/2007 |
| DE | 4334037 | 4/1995 |
| DE | 19500550 | 7/1996 |
| DE | 19855521 | 6/2000 |
| DE | 19855521 A1 | 6/2000 |
| EP | 0884061 | 12/1998 |
| EP | 0884061 A | 12/1998 |
| EP | 0922465 | 6/1999 |
| EP | 1267981 BI | 4/2000 |
| EP | 1005877 A2 | 6/2000 |
| EP | 1135184 | 6/2000 |
| EP | 07795681.1 | 6/2007 |
| EP | 2029210 | 3/2009 |
| EP | 09726613.4 | 3/2009 |
| EP | 2276534 | 1/2011 |
| GB | 1402255 | 8/1975 |
| GB | 2168256 A | 6/1986 |
| GB | 2326099 | 12/1998 |
| GB | 2344528 | 6/2000 |
| JP | 2009516497 | 6/2007 |
| JP | 2009540922 | 11/2009 |
| WO | WO 95/22367 | 8/1995 |
| WO | WO9522367 | 8/1995 |
| WO | WO 00/27461 | 5/2000 |
| WO | WO0027461 | 5/2000 |
| WO | WO 00/32262 | 6/2000 |
| WO | WO 00/32262 A1 | 6/2000 |
| WO | WO0197890 | 12/2001 |
| WO | WO 03/045487 A2 | 6/2003 |
| WO | WO 2004/067262 | 8/2004 |
| WO | WO2004089453 | 10/2004 |
| WO | WO 2004/101046 A1 | 11/2004 |
| WO | WO2004101046 | 11/2004 |
| WO | WO 2006/023486 | 3/2006 |
| WO | WO2007149202 | 12/2007 |
| WO | WO2007149203 | 12/2007 |
| WO | WO2007149301 | 12/2007 |
| WO | WO2009123835 | 10/2009 |

OTHER PUBLICATIONS

Dullenkopf, et al., "Fluid leakage past tracheal tube cuffs: evaluation on the new Microcuff endotracheal tube," *Intensive Care Medicine*, (2003) vol. 29, pp. 1849-1853.

Ayçe Gönen Karakeçili et al.; "Comparison of Bacterial and Tissue Cell Initial Adhesion on Hydrophilic/Hydrophobic Biomaterials," J Biomater. Sci. Polymer Edn, vol. 13, No. 2, pp. 185-196 (2002).

Blunt et al.; "Gel Lubrication of the Tracheal Tube Cuff Reduces Pulmonary Aspiration," 2001 American Society of Anesthesiologists, Inc. Lippincott Williams & Wilkins, Inc.; Anesthesiology, V. 95, No. 2, Aug. 2001.

Shintani; "Modification of Medical Device Surface to Attain Anti-Infection," National Institute of Health Sciences; Trends Biomater. Artif. Organs, vol. 18(1), pp. 1-8 (2004).
Sartomer Application Bulletin; "Functional Acrylic Monomers as Modifiers for PVC Plastisol Formulations," pp. 1-6.
Batchelder, P.B., *S-233—Seal Effectiveness of Seven Endotracheal Tube Cuff Designs: A Study Using an In Vitro Model Trachea*, http://www.abstractsonline.com/Plan/AbstractPrintView.aspx?mID=2481& sKey=78a49ea . . . Mar. 17, 2010.
U.S. Appl. No. 11/473,362, filed Jun. 22, 2006, Donald S. Nelson.
U.S. Appl. No. 12/059,556, filed Mar. 31, 2008, Donald S. Nelson.
Dave et al., *Respiration and the Airway—Effect of tracheal tube cuff shape on fluid leakage across the cuff: an in vitro study*, British Journal of Anaesthesia 105 (4) 538-43 (2010).
Dullenkopf, et al., *Fluid leakage past tracheal tube cuffs: evaluation of the new microcuff endotracheal tube*, Intensive Care Med 29:1849-1853 (2003).
K090352—Covidien Special 510(k) Summary, (Apr. 3, 2009).
King et al., *Tracheal tube cuffs and tracheal dilation*, CHEST® 67; 458-462 (1975).
Kollef, et al., *Silver-Coated Endotracheal Tubes and Incidence of Ventilator-Associated Pneumonia*, The NASCENT Randomized Trial, 2008 American Medical Association, reprinted JAMA, vol. 300, No. 7, pp. 805-813; Aug. 20, 2008.
Lichtenthal et al., *Respiratory—Airway Management, A89—Do Endotracheal Tubes Prevent Microaspiration*? (Undated).
Mahul et al., *Prevention of nosocomial pneumonia in intubated patients: respective role of mechanical subglottic secretions drainage and stress ulcer prophylaxis*, Intensive Care Med 18:20-25 (1992).
Mallinckrodt™ TaperGuard™ Endotracheal Tubes Manage secretions more effectively in the operating room; Covidien (undated).
Mecca et al., *Benchtop comparison: Fluid sealing performance of barrel-shaped versus taper-shaped polyvinyl chloride (PVC) high volume, low-pressure endotracheal tube cuffs* Oct. 2008.
Molnlycke Steritex, *Facts about the NL-Tube with Cuff-Inflator*—the tracheostomy system with controlled cuff pressure (undated).
Mulier et al., *Evaluation of Silent Aspiration in Morbid Obese Patients during Laparoscopic Gastric Bypass Surgery*, Oct. 17, 2010; http://www.asaabstracts.com/strands/asaabstracts/printAbstract.htm;jsessionid=C1C176AF . . . Aug. 4, 2010.
Oikkonen et al., *Apparatus Leakage of fluid around low-pressure tracheal tube cuffs*, Anesthesia (1997) 52:567-569, Blackwell Science Ltd. (1997).
Petring et al., *Prevention of Silent Aspiration Due to Leaks around Cuffs of Endotracheal Tubes*, Anesth Analg 65:777-80 (1986).
Seegobin, et al., *Endotracheal cuff pressure and tracheal mucosal blood flow: endoscopic study of effects of four large volume cuffs*, British Medical Journal, vol. 288, pp. 965-968; Mar. 31, 1984.
Seegobin, Ronald D. and Van Hasselt, Gillian L., *Aspiration beyond endotracheal cuffs*, Can Anaesth. Soc. J. 33:3/pp. 273-279 (1986).
Sheridan® Endotracheal Tubes—Hudson RCI—Breathing made easier (2002).
Sittig, Steven E. and Pringnitz, James E., *Tracheostomy: Evolution of an Airway*, AARC Times, (Feb. 2001) pp. 48-51.
TaperGuard® product literature (undated).
510(k) Summary (Revised), May 9, 2012.
Batchelder, et al.; "Leak Rates of 3 ET Tube Cuff Designs over a Range of Artificial Trachea Sizes and Cuff Pressures," Abstracts of the American Society of Anesthesiologists, 2011.
File History of U.S. Appl. No. 11/473,362, filed Jun. 22, 2006, Nelson, Donald S.
File History of U.S. Appl. No. 12/059,556, filed Mar. 31, 2008, Nelson, Donald S.
File History of U.S. Appl. No. 13/612,381, filed Sep. 12, 2012, Nelson, Donald S.
File History of U.S. Appl. No. 13/612,397, filed Sep. 12, 2012, Nelson, Donald S.
File History of Japanese Patent Application No. JP2009516497, filed Jun. 1, 2007.
File History of European Patent Application No. EP07795681.1, filed Jun. 1, 2007.
File History of European Patent Application No. EP09726613.4, filed Mar. 10, 2009.
File History of Canadian Patent Application No. CA20072654938, filed Dec. 9, 2008.
Truscott, W., "*The Strengths and Weaknesses of Endotracheal Tube Cuffs*", Infection Protection (Aug. 2009).
Karlnoski et al., "*Low-Pressure Microcuff Adult Endotracheal Tube Reduces the Incidence of Ventilator-Associated Pneumonia*", Poster 19; Clinical Abstract, microcuff reduces vap, tampa general study, ASCCA meeting (Oct. 2009).
Rose et al., "*Microaspiration and Endotracheal Tube Cuff Leakage; a Bench Study Comparing Polyurethane and Polyvinyl Chloride Endotracheal Tube Cuff Design*", Texas Health Presbyterian Hospital, Dallas (2009).
Marcus, "*Study: Overblown Cuffs Common During Surgery—UK Analysis Finds Averages Well Above Recommended Limit*", Anesthesiology News, Issue: Oct. 2009/vol. 35:10; http.//www.anesthesiologynews.com/printview.asp?article_id= . . . .
Fine et al., "New Advances in Pediatric Ventilation: Revolutionizing the Management of Pediatric Intubation with Cuffed Tubes", Pediatric Microcuff Endotracheal Tube 2006.
Swiss Medical Weekly, Supplement 166, The European Journal of Medical Sciences, Annual Meeting—Swiss Society of Anaesthesiology and Resuscitation (2008).
Weiss et al., "Prospective Randomized Controlled Multi-Centre Trial of Cuffed or Uncuffed Endotracheal Tubes in Small Children," Paediatrics, British Journal of Anaesthesia 103(6): 867-73 (Dec. 2009).
Gerber et al., "Cuffed tubes for infants and children in anaesthesia and intensive care: Why we should change to cuffed tubes in paediatric airway management," Review Article, Journal of Paediatric Respiratory and Critical Care (Dec. 2008).
Batchelder et al., Leak Rates of Three Endotracheal Tube Cuff Designs over a Range of Artificial Trachea Sizes and Cuff Pressures (2010).
Kimberly-Clark KimVent*, VAP Solutions—Helping you protect your patients fromVAP (2010).
Kimberly-Clark Microcuff* Endotracheal Tube—Revolutionary cuff material designed to reduce micro-aspiration, Ventilator-Associated Pneumonia, Kollef, et al. Respiratory Care, 2005.
Kimberly-Clark Microcuff* Pediatric Endotracheal Tube, Finally a cuffed ET tube designed for the pediatric anatomy, Weiss et al. Br J. Anaesthesia 2005.
Miller et al., "A Polyurethane Cuffed Endotracheal Tube (PUC-ETT) Was Associated with Decreased Rates of Ventilator-Associated Pneumonia", Univ. Of Michigan Health System, Div. of Pulmonary and Critical Care Medicine (2009).
2009 Press Release—Kimberly-Clark Health Care Microcuff Pediatric ET tube—Clinical Study Shows Benefit of Cuffed Over Uncuffed Endotracheal Tubes in Pediatric Patients (Roswell, GA—Jan. 7, 2009).
2009 Press Release—Kimberly-Clark Microcuff Adult Endotracheal Tube Shown to Reduce the Incidence of Ventilator-Associated Pneumonia (Roswell, GA—May 19, 2009).
Kimberly-Clark Microcuff Adult Endotracheal Tubes—Product Technical Update: Cuff Condensation.

* cited by examiner

ENDOTRACHEAL CUFF AND TECHNIQUE FOR USING THE SAME

BACKGROUND OF THE INVENTION

1. Field of the Invention

The present invention relates to medical devices, and more particularly, to airway products, such as tracheal tubes and cuffs.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the course of treating a patient, a tube or other medical device may be used to control the flow of air, food, fluids, or other substances into the patient. For example, medical devices such as tracheal tubes may be used to control the flow of one or more substances into or out of a patient. In many instances it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

For example, tracheal tubes may be used to control the flow of air or other gases through a patient's trachea. Such tracheal tubes may include endotracheal (ET) tubes, tracheostomy tubes, or transtracheal tubes. To seal these types of tracheal tubes, an inflatable cuff may be associated with these tubes. When inflated, the cuff generally expands into the surrounding trachea to seal the tracheal passage around the tube.

However, to fit a range of trachea anatomies and to provide low intra cuff pressure, cuff diameters are usually about one and a half times the diameter of the average trachea. Therefore, when inserted in an average-sized trachea, such a cuff is unable to fully expand and will fold in on itself within the trachea. These folds may serve as leak paths that allow mucosal secretions to flow past the cuff and enter the lung.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

There is provided an inflatable balloon cuff that includes a proximal opening and a distal opening in a wall of the balloon cuff; and a tapered section along at least 50% of the length along an axis of the inflated balloon cuff, wherein the tapered section comprises a taper angle of at least 15 degrees, measured as an included angle of at least a portion of the tapered section and an imaginary axis connecting the proximal opening and the distal opening.

There is also provided a method of manufacturing an inflatable balloon cuff that includes providing a proximal opening and a distal opening in a wall of the balloon cuff; and providing a tapered section along at least 50% of the length along an axis of the inflated balloon cuff, wherein the tapered section comprises a taper angle of at least 15 degrees, measured as an included angle of at least a portion of the tapered section and an imaginary axis connecting the proximal opening and the distal opening.

There is also provided an inflatable balloon cuff that includes a tapered section, wherein a balloon wall of the tapered section is of continuously varying thickness along the tapered section such that the balloon wall at the widest point of the tapered section is thinner than the balloon wall at the narrowest point of the tapered section.

There is also provided a method of manufacturing an inflatable balloon cuff that includes providing an inflatable balloon cuff having a tapered section, wherein a balloon wall of the tapered section is of continuously varying thickness along the tapered section such that the balloon wall at the widest point of the tapered section is thinner than the balloon wall at the narrowest point of the tapered section.

There is also provided an inflatable balloon cuff that includes a tapered section, wherein at least a portion of the tapered section is adapted to form a wrinkle-free band against a patient's tracheal wall when inflated.

There is also provided a method of manufacturing an inflatable balloon cuff that includes providing an inflatable balloon cuff having a tapered section, wherein at least a portion of the tapered section is adapted to form a wrinkle-free band against a patient's tracheal wall when inflated.

There is also provided an inflatable balloon cuff that includes a tapered section comprising at least a portion of the balloon cuff, wherein at least a portion of the balloon walls in the tapered section are less than 60 microns in thickness.

There is also provided a method of manufacturing an inflatable balloon cuff that includes providing an inflatable balloon cuff having a tapered section comprising at least a portion of the balloon cuff, wherein at least a portion of the balloon walls in the tapered section are less than 60 microns in thickness.

There is also provided an inflatable balloon cuff that includes a proximal opening and a distal opening in a wall of the balloon cuff; a first tapered section along an imaginary axis connecting the proximal opening and the distal opening of the inflated balloon cuff; and a second tapered section along the imaginary axis connecting the proximal opening and the distal opening.

There is also provided an inflatable balloon cuff that includes a tapered section, wherein a balloon wall of the tapered section is of constant along the tapered section.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to provide a medical balloon, such as an endotracheal cuff or other medical device, which may substantially seal the passage in which the cuff is inserted so that mechanical ventilation can be used to introduce air, oxygen, or medications into the lungs. In accordance with some aspects of the present technique, a medical balloon with a tapered shape is provided that is adapted to be used with an endotracheal tube or device.

The tapered balloon cuffs provided herein may provide advantages over a typical cuff. A typical inflatable cuff generally assumes a cylindrical or barrel shape when inflated that may include short tapered or partially tapered sections designed to connect the ends of the cuff to a narrower object, such as an endotracheal tube. Thus, a generally cylindrical cuff has a constant diameter along most of its length when fully inflated. This diameter is typically larger than the size of the tracheal passage. Therefore, when a typical cylindrical cuff is inserted into a patient's trachea and inflated, the cuff walls of the cylinder are unable to inflate to their maximum diameter and may fold in on themselves, which may cause wrinkles and leak paths to form.

A tapered cuff provides an improved seal against a patient's passage. Tapered cuffs include at least one section with a tapered shape. The tapered section includes a section that comes into direct contact with a patient's trachea. It should be understood that, in certain embodiments, the tapered section may be only a portion of the entire cuff. The tapered shape of the cuffs as provided herein results in the cuff displaying a range of inflated cuff diameters along the axis of the patient's passage. This range of cuff diameters results in at least one region along the inflated cuff that is substantially equal in diameter to a patient's trachea. The portion of the tapered cuff with a diameter that is substantially sized to the diameter of the trachea provides a relatively higher quality seal against the trachea that is substantially wrinkle-free.

The tapered shape of the cuffs as provided herein may be characterized by the cuff diameters at both ends of the taper. For example, the tapered shape may be described by providing the cuff diameter at the widest point of the taper as well as the cuff diameter at a narrower point. It should be understood that cuff diameters may be measured when the cuff is fully inflated while not inserted in a patient trachea along an axis that is substantially orthogonal to the axis of the endotracheal tube. A cuff diameter may be measured from cuff wall to cuff wall, either exterior wall to exterior wall or interior wall to interior wall. In certain embodiments, the taper may range from two times the size of an average trachea at the widest point to half the size of the average trachea or smaller at the narrowest part of the taper. It should be understood that an average trachea size may be an adult male or female average size that is based on height and weight, or a child average size. For example, an adult trachea may range in size from 14 mm to 27 mm, with the average being around 20 mm. Women typically use a size 7.0 to 7.5 endotracheal tube, while men may use a size 7.5 to 8.0 endotracheal tube. The size of the tube typically refers to the inside diameter of the main airway tube. In specific embodiments, the tapered region may narrow from a widest cuff diameter of 1.355 inches to a narrower diameter of 0.65 inches or smaller. It is envisioned that a single cuff may be designed to accommodate a wide variety of tracheal sizes along a single taper. Thus, a further advantage of a tapered cuff may be its adaptability to patients of a variety of sizes. In one embodiment, certain smaller diameters at the narrow end of the cuff taper are associated with increased sealing performance. For example, certain smaller diameters at the narrow end may maintain the sealing band of the cuff around the trachea even though the tube itself may not be centered in the trachea. Due to the curvature typically built into tracheal tubes for ease of insertion and patient comfort, the tube does not necessarily stay centered in the trachea. By having smaller diameters at the narrow end, it is possible to maintain the benefits of the tapered shape even when the tube is not symmetrically located within the trachea. Thus, in certain embodiments it may be desirable to have cuff diameters less than 0.65 inches or less than 0.60 inches at the narrow end of the cuff. The cuff diameters may be even smaller for smaller patients, such as pediatric patients, and in certain embodiments may only be limited by the outer diameter of the tubing that is sufficient to achieve acceptable ventilation of the patient.

In other embodiments, the tapered region of the tapered cuff may be characterized by the slope or angle of the taper, which is the included angle of the tapering cuff wall and the axis of an attached endotracheal tube. For example, the angle of the taper may include a tapering angle of at least 15 degrees, at least 20 degrees, or at least 25 degrees. In a specific embodiment, the angle of the taper may be between 17 and 20 degrees. Providing tapering angles greater than 15 degrees generally indicates a greater variance between the widest point and the narrower point of the taper. Further, the tapered region of the tapered cuff may be characterized in certain embodiments by the rate of tapering from the widest point of the taper to a narrower point. A cuff may exhibit a continuous rate of tapering, or a linear tapering, from a wider diameter to a narrower diameter. Cuffs with linear tapering may be less costly to manufacture. In other embodiments, the taper may have a nonlinear rate of tapering. For example, it may be advantageous to provide stepwise tapering along the cuff, whereby a certain cuff diameter is maintained for 5-10 mm along the length of the taper. The taper may also be characterized by a monotonically decreasing function, such as a hyperbola. Additionally, a taper may be characterized by its length along the axis of an endotracheal tube. For example, a taper may be along at least 30%, at least 40%, at least 50%, at least 75%, or at least 95% of the length of the cuff along a specific axis.

Tapered medical cuffs as provided herein may be used in conjunction with any suitable medical device. In certain embodiments, the tapered cuffs as provided herein may be used in conjunction with a catheter, a stent, a feeding tube, an intravenous tube, an endotracheal tube, a tracheostomy tube, a circuit, an airway accessory, a connector, an adapter, a filter, a humidifier, a nebulizer, or a prosthetic, in various embodiments.

Figure 1:
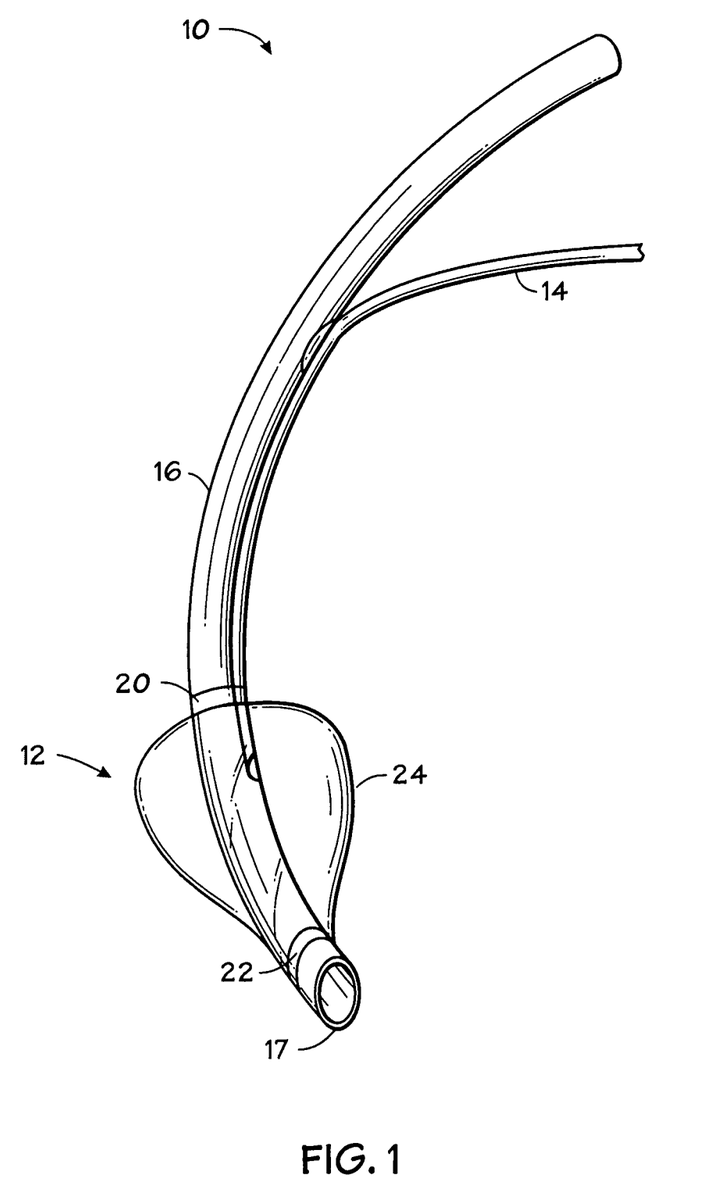
FIG. 1 illustrates an endotracheal tube with an inflatable balloon cuff in accordance with aspects of the present technique.

An example of a tapered cuff used in conjunction with a medical device is a cuffed endotracheal tube 10, depicted in FIG. 1. The cuffed endotracheal tube 10 includes an inflatable tapered cuff 12 that may be inflated to form a seal against the trachea wall 28 (see FIG. 2). The tapered cuff is disposed on an endotracheal tube 16 that is suitably sized and shaped to be inserted into a patient and allow the passage of air through the endotracheal tube 16. Typically, the cuff is disposed, adhesively or otherwise, towards the distal end 17 of the endotracheal tube 16. The tapered cuff 12 may be inflated and deflated via a lumen 14 in communication with the tapered cuff 12, typically through a hole or notch in the lumen 14. The tapered cuff 12 may generally have an amorphous, or irregular, shape in the uninflated state and may assume the tapered shape when inflated. The tapered cuff 12 has a proximal opening 20 and a distal opening 22 formed in the cuff walls 24 sized to accommodate the endotracheal tube 16. The proximal opening 20, located closer to the "machine end" of the tube 16, and a distal opening 22, located closer to the "patient end" of the tube 16, are typically used to mount the cuff 12 to the tube 16.

The tapered cuff 12 may be formed from materials having suitable mechanical properties (such as puncture resistance, pin hole resistance, tensile strength), chemical properties (such as forming a suitable bond to the tube 16), and biocompatibility. In one embodiment, the walls of the inflatable cuff 12 are made of a polyurethane having suitable mechanical and chemical properties. An example of a suitable polyurethane is Dow Pellethane® 2363-90A. In another embodiment, the walls of the inflatable cuff 12 are made of a suitable polyvinyl chloride (PVC). Other suitable materials include polypropylene, polyethylene teraphthalate (PETP), low-density polyethylene (LDPE), silicone, neoprene, polyisoprene, or polyurethane (PU).

Figure 2:
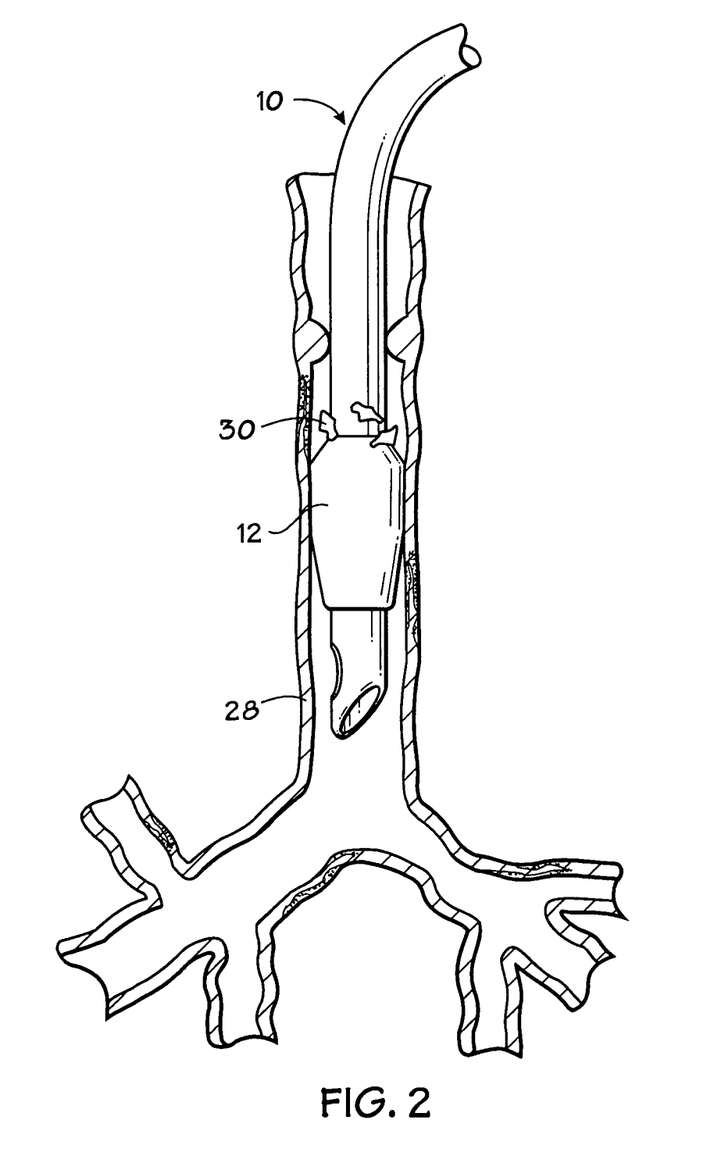
FIG. 2 illustrates the inflatable balloon cuff of the present techniques inserted into a patient's trachea.

FIG. 2 shows the exemplary cuffed endotracheal tube 10 inserted into a patient's trachea. The tapered cuff 12 is inflated to form a seal against the tracheal walls 28 and may prevent secretions 30 or other detritus from passing through the trachea into the lungs. The tapered cuff 12 assumes a partially tapered shape when inserted in the patient's trachea, as described in more detail in FIGS. 3-6.

Figure 3:
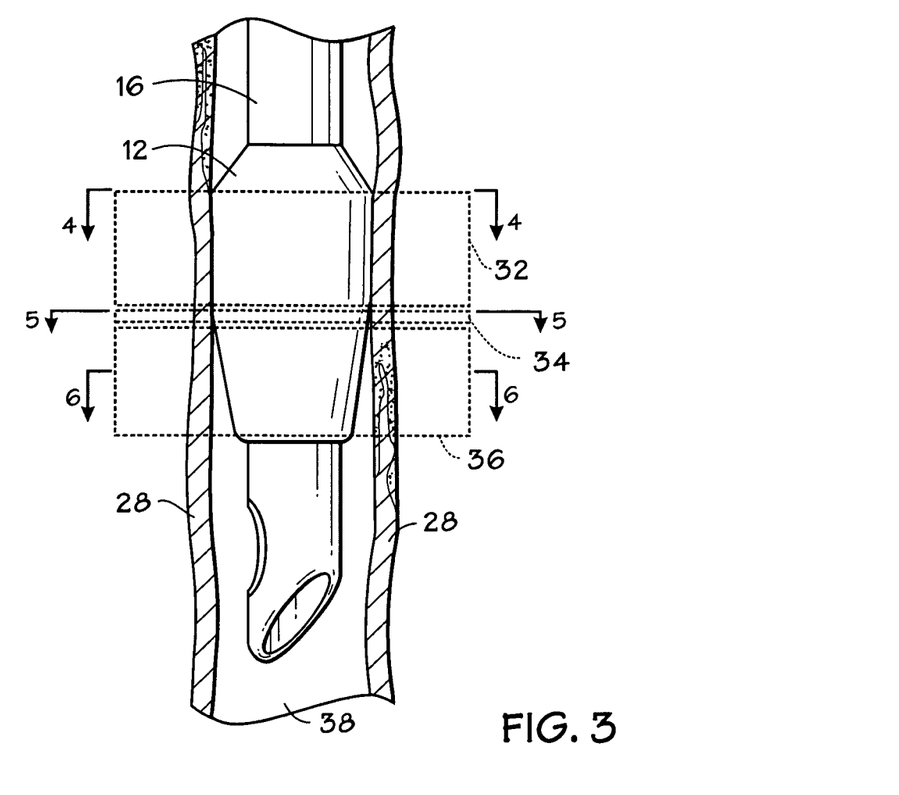
FIG. 3 illustrates three different regions of the balloon cuff of the present techniques after insertion into a patient's trachea.

As depicted in FIG. 3, the tapered shape of the cuff 12 may result in different regions of the tapered cuff 12 interacting with the trachea in a variety of manners. One portion of the tapered cuff 12 includes cuff walls with fully inflated diameters larger than the diameter of the tracheal passage 38. As the cuff walls of this region inflate within the trachea, they encounter the tracheal walls 28 and are prevented from assuming their fully inflated diameters, as is normally the case with high volume low pressure cuffs. Thus, the tapered cuff in this region may be partially flattened against the tracheal walls 28 to create a wrinkled region 32 of the cuff (see FIG. 4). A portion of the tapered cuff 12 that includes cuff walls with diameters substantially equal to the diameter of the tracheal passage 38 may form a wrinkle-free band 34 (see FIG. 5) against the tracheal walls 26, as in this region of the tapered cuff 12, the cuff walls assume their fully inflated diameters. The region 36 of the tapered cuff 12 with a diameter smaller than the passage may form a minimal contact or no contact region 36 (see FIG. 6) with the tracheal walls.

Figure 4:
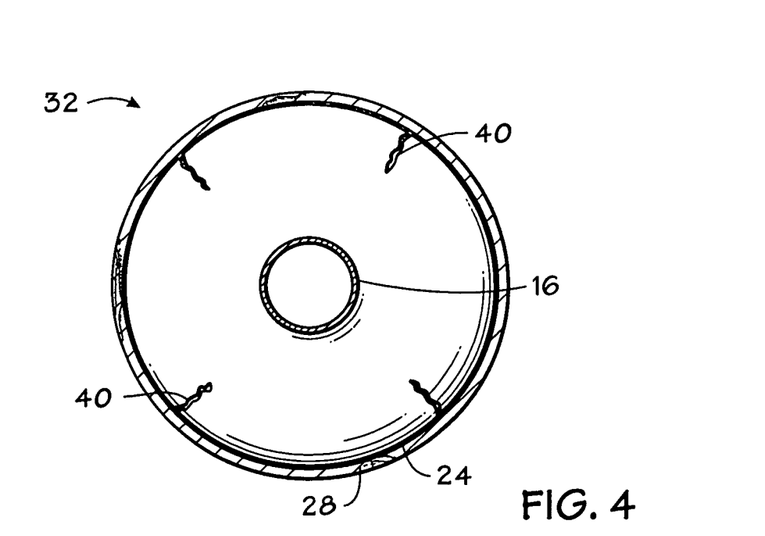
FIG. 4 is a top view of the wrinkled region of the balloon cuff of FIG. 3.

FIG. 4 depicts a top view of cross-section through the wrinkled region 32 of an inserted tapered cuff 12. As depicted, the cuff walls 24 may be unable to inflate to their fully inflated diameters in the tracheal passage. In order to fit into the passage, the flexible cuff walls 24 of the tapered cuff 12 fold in on each other and may form multiple wrinkles 40. It should be understood that, depending on how a cuffed endotracheal tube 10 is inserted into the trachea, the tapered cuff 12 may not be completely centered within the tracheal passage.

Figure 5:
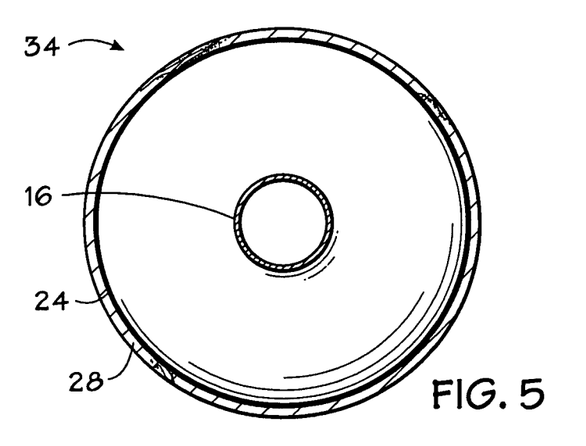
FIG. 5 is a top view of the wrinkleless band region of the balloon cuff of FIG. 3.

FIG. 5 depicts a top view of a cross-section through the region of the substantially wrinkle-free band 34 of the tapered cuff 12. The wrinkle-free band 34 is formed in the region of the cuff 12 where the cuff diameter is substantially equal to the patient's trachea. The wrinkle-free band 34 also includes a small part of the cuff 12 with cuff diameters that are only slightly larger than the tracheal diameter, as this part of the cuff does not include cuff diameters that are large enough to support wrinkling or folding. As shown, the cuff walls are generally flush against the tracheal walls 28. As the tracheal walls 28 may be slightly irregular, the wrinkle-free band may vary from patient to patient. Because of the irregular shape of the trachea and the fact that the tube may not be centered radially, the wrinkle-free band 34 may have varying width around its outer diameter as well as have its center vary axially as a function of angular position in the trachea. For example, the plane of the wrinkle-free band 34 may have varying angles, including angles 0-45 degrees off-axis from an axis orthogonal to the patient's trachea. The wrinkle-free band 34 may be characterized by its length along the axis of the tube 16, or along the axis of the patient's trachea. In certain embodiments, the wrinkle-free band 34 provides wrinkle-free contact of least 1 mm along the patient's trachea. In specific embodiments, the wrinkle-free band ranges from 1 mm to 3 mm in size, or from 3 mm to 6 mm in size.

Figure 6:
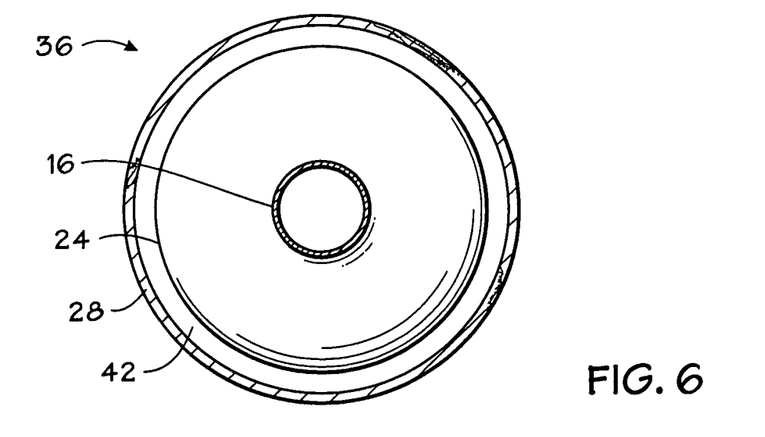
FIG. 6 is a top view of the minimal contact region of the balloon cuff of FIG. 3.

FIG. 6 depicts a top view of a cross-section through the region 36 of the tapered cuff 12 in which the cuff wall diameters are smaller than tracheal diameter. In this minimal contact region 36, the cuff walls are generally not in contact with the patient's tracheal walls, leaving a gap 42 that increases in size as the cuff wall diameter decreases. This arrangement may provide additional advantages related to patient comfort. As a substantial region of the tapered cuff does not contact the trachea walls 28 during use, tracheal tissue irritation may be minimized.

Figure 7:
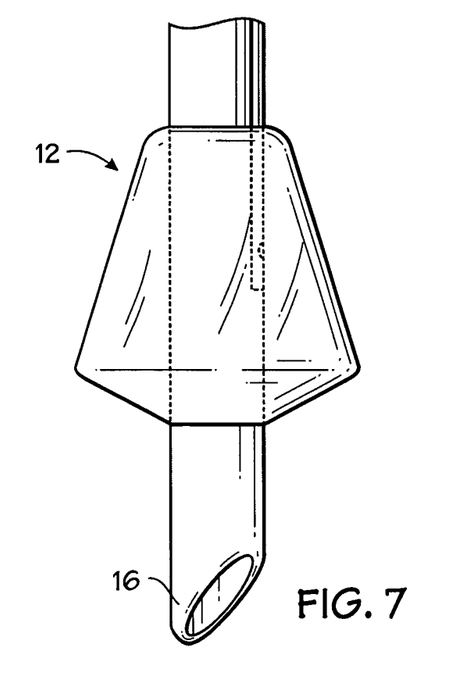
FIG. 7 illustrates an alternate configuration of the balloon cuff of the present techniques in which the cuff tapers towards the proximal end of the conduit.
Figure 8:
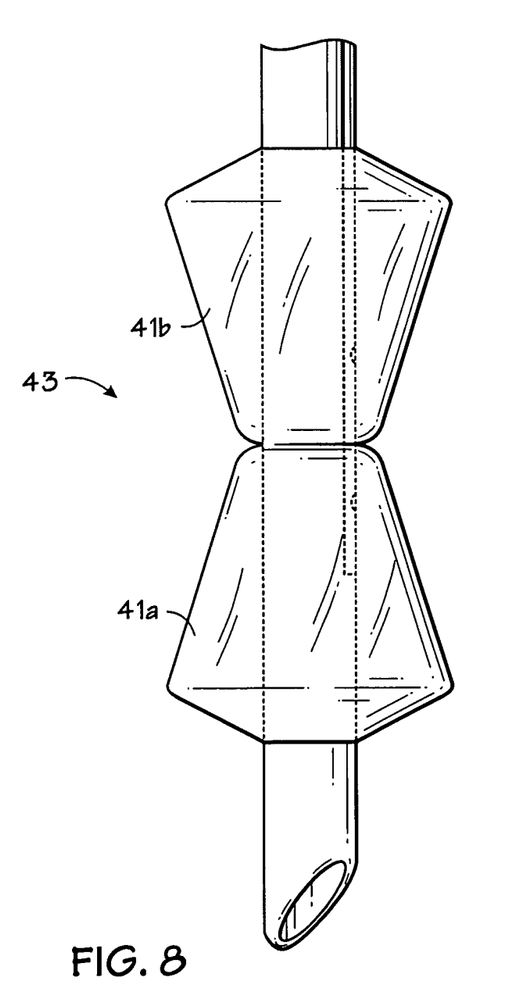
FIG. 8 illustrates an alternate configuration of the balloon cuff of the present techniques having a generally hourglass configuration.
Figure 9:
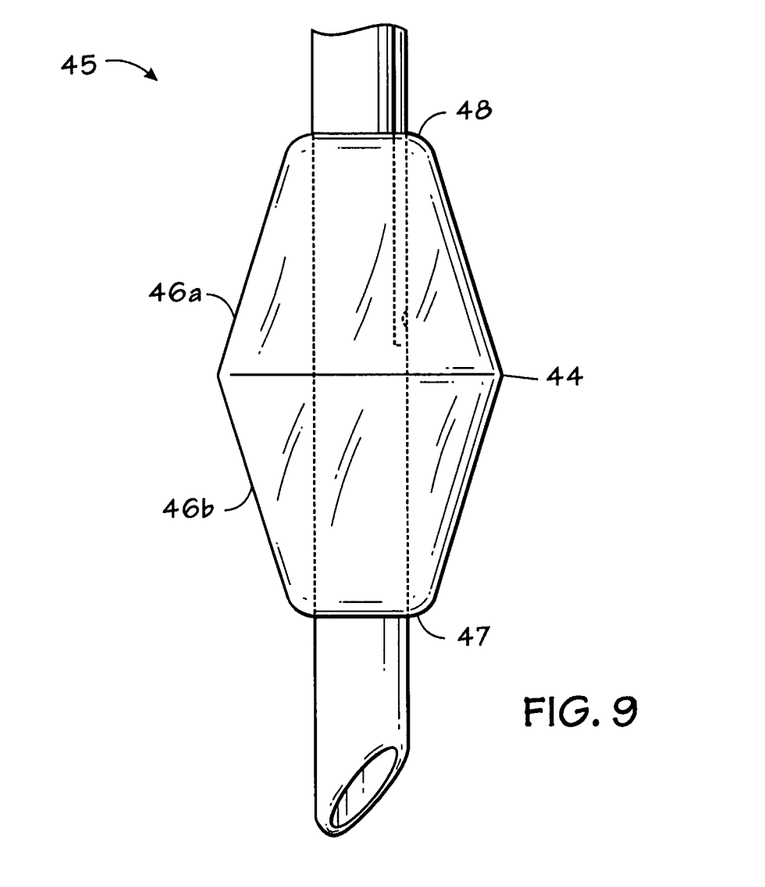
FIG. 9 illustrates an alternate configuration of the balloon cuff of the present techniques having a generally diamond-like configuration.

It is also envisioned that a tapered cuff 12 as provided herein may taper away from the distal end of the conduit 16, as shown in FIG. 7. Such an arrangement may provide similar advantages to the taper cuff 12 that tapers towards the distal end of the conduit 16 as provided herein. In other embodiments the inflatable cuff 12 may assume a variety of tapered shapes when inflated. For example, referring now to FIGS. 8 and 9, various exemplary cuff shapes are depicted. FIG. 8 depicts an exemplary cuff 43 having a generally hourglass shape, i.e., two tapered sections 41A and 41B generally connected at their apexes. Similarly, FIG. 9 depicts an exemplary cuff 45 with tapered sections 46A and 46B that is wider at the midsection 44 of the tapered sections 46 than at the proximal end 48 or the distal end 47, i.e., two cones generally connected at their bases. It is envisioned that cuff 43 and cuff 45 may provide the advantage of providing dual wrinkle-free bands along the tracheal walls when inserted into a patient's trachea. The dual bands may provide improved sealing by providing greater total wrinkle-free contact are with the tracheal walls. In certain embodiments, additional cuff shapes that may form multiple wrinkle-free bands are also contemplated. As will be appreciated by those of ordinary skill in the art, other cuff shapes are within the scope of the present disclosure.

The tapered cuffs 12 as provided herein may include cuff walls 24 with constant or varying wall thicknesses along the length of the taper. Cuff wall thickness may vary from the widest part of the taper to the narrowest part of the taper. In certain embodiments, it is advantageous to specify cuff wall thickness variation because certain cuff wall thicknesses in the wrinkle-free band 34 may help to terminate the folds that are present in the wrinkled region 32 of the tapered cuff 12 (as in FIG. 3-FIG. 6). Thicker cuff walls tend to be less flexible than thinner cuff walls, and thus less likely to form wrinkles. If the walls of the wrinkle-free band 34 are thicker than the walls of the wrinkled region 32, the wall thickness may aid in the termination of the wrinkles. Certain wall thicknesses may be associated with wrinkles that are more easily terminated by the "band" that forms at the point where the cuff diameter matches the trachea. In certain embodiments, it is contemplated that at least a portion of the cuff walls in the tapered region of the cuff are less than 60 microns in thickness. In another embodiment, the cuff walls are between 10 microns and 3 millimeters in thickness. In certain embodiments, the cuff walls are between 0.5 mils (where mils are thousandths of an inch) and 3 mils. In specific embodiments, the cuff walls vary along the length of the taper from between 2 microns to 140 microns in thickness, from between 20 microns to 60 microns in thickness, and from between 30 microns to 50 microns in thickness. In certain embodiments, it may be advantageous to provide a cuff 12 with a constant thickness, This thickness specification may be accomplished in a number of ways. For example, in one embodiment, the tapered cuffs may be manufactured by a blow molding process or extrusion blow molding process. For example, the cuffs may also be made by using preextruded tubing and applying heat and pressure appropriately within a molding cavity to achieve the desired shape (blow molding). These cuffs can also be formed by extrusion blowmolding, wherein an extruder fed polymer pellets melts the polymer and feeds the molten polymer through a die to form a tube shape. This still molten polymer is then captured in a mold and air pressure is applied to expand the tube out to the walls of the mold, thus achieving the desired shape. In the extrusion blow molding process, a core or mandrel of the extruder has apertures to admit a gas such as pressurized air or an inert gas like nitrogen, into the medical device in the neighborhood of the cuff. After a length of medical device has been extruded, a mold clamps the medical device around the mandrel. As gas is admitted to the cuff area through the mandrel, the cuff expands against the mold. In the alternative, the cuff wall may be expanded in a second discrete expansion process following an extrusion or molding process, such as with a shuttle blow molding process. After initial extrusion, the extruded cuff will have a generally tubular shape with a substantially uniform wall thickness. This tubular shape may then be blown into the tapered shape. This process results in the area of the cuff with larger diameters having thinner walls because the same amount of material is stretched over a larger area. In an alternate embodiment, the wall thickness, constant or variable, along the length of the taper may be specified in the blow molding process by using a programmable parasin on the extruder. A programmable parasin allows the wall thickness being extruded to be controlled as a function of length. Therefore, the extruded section may have walls of varying thickness. This extruded section may then be blowmolded as described above. Other cuff shapes and designs are discussed in the U.S. patent application Ser. No. 11/473,362 titled "ENDOTRACHEAL CUFF AND TECHNIQUE FOR USING THE SAME" to Donald S. Nelson and Dhairya Mehta filed on Jun. 22, 2006, the U.S. patent application Ser. No. 11/473,915 titled "ENDOTRACHEAL CUFF AND TECHNIQUE FOR USING THE SAME" to Seamus Maguire, Sean Morris, Paul O'Neill, and Patrick Joseph Tiernan filed on Jun. 22, 2006, and the U.S. patent application Ser. No. 11/473.285 titled "THIN CUFF FOR USE WITH MEDICAL TUBING AND APPARATUS FOR MAKING THE SAME" to Joel Colburn and Roger Caluya filed on Jun. 22, 2006, which are hereby incorporated by reference in their entirety.

Figure 10:
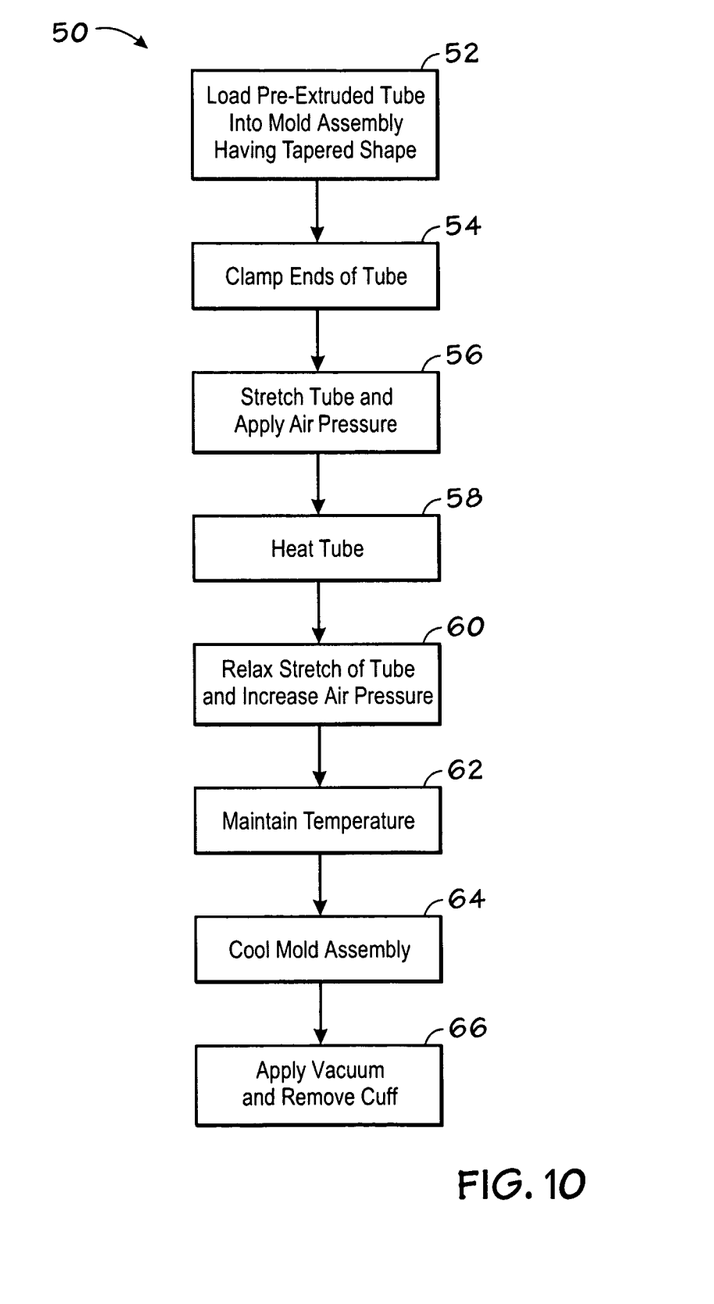
FIG. 10 is a flowchart depicting a blowmolding method of manufacturing a balloon cuff of the present techniques.

One example of such a suitable blow molding process 50 is depicted in the flowchart of FIG. 10. In this example, a tube, such as an extruded polyurethane tube, is loaded (block 52) into a blowing machine or mold assembly with a tapered shape, such as a machine used to blow angioplasty balloons. As described above, the extruded tube may have walls of varying thickness. Balloon blowing machines typically allow process parameters such as extrusion stretch, blow pressure, and temperature to be controlled. Once loaded, the mold assembly is closed, and the tube is clamped at each end (block 54). The tube is stretched and air is blown into the tube via an air conduit, such as an air hose or nozzle, connected to a source of pressurized air, such as an air pump or pre-pressurized source, to achieve a desired positive pressure within the tube (block 56). Heat is applied to the tube (block 58), such as via heating elements integral to the mold assembly. As the heat is applied, the stretch of the tube is relaxed and the air pressure within the tube is increased (block 60). Once the desired temperature is reached it is maintained for an interval of time (block 62). Afterward, the temperature of the mold assembly is allowed to drop or is actively cooled (block 64). A vacuum is applied within the tube, which now includes the blown cuff, to release the tube and cuff from the mold assembly and the tube and cuff are removed from the mold assembly (block 66).

For example, in one particular implementation a commercially available extrusion of Dow Pellethane® 2363-90A having an inner diameter of 0.239±0.005 inches (6.0706±0.127 mm) and a wall thickness of 0.008 inches (0.2032 mm) may be blown to form a cuff 12 suitable for use with a 7.5 mm internal diameter (ID) endotracheal tube. The extruded tube may be stretched 50 to 100 mm on each end and a pressure of 1.0 to 2.0 bar is applied within the extruded tube. The extruded tube is heated for 50 to 100 seconds. As the temperature ramps up, the stretched ends of the extruded tube are relaxed to 20 to 70 mm and the air pressure within the extruded tube is increased to 1.5 to 2.1 bar. The temperature is allowed to increase to 120 to 150° C., where it is maintained for 10 to 30 seconds. The mold assembly is then cooled to 40 to 55° C., a vacuum is applied to the molded extrusion and cuff, and the extrusion and cuff are removed from the mold assembly. In another embodiment, the cuff wall thickness may be controlled by a dip coating process (not shown). For example, by controlling the withdrawal rate of a cuff mandrel from a dip coating solution, the wall thickness can be controlled. Using this control or multiple dips, it is possible to obtain even step function changes in wall thickness.

Figure 11:
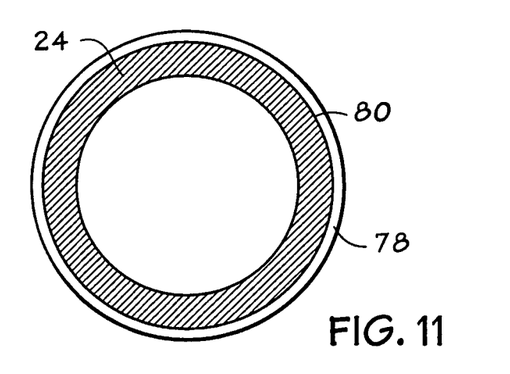
FIG. 11 illustrates a balloon cuff of the present techniques with an antimicrobial layer.

In certain embodiments, it may be desirable for the tapered cuff to include an antimicrobial surface to prevent the adhesion and propagation of biofilms. As shown in FIG. 11, a wall 24 of a cuff 12 may be a hydrophobic polymer with an outer antimicrobial layer 78 that includes a hydrophilic polymer and an antimicrobial compound disposed on an outer surface 80 of the cuff wall 24. The antimicrobial layer may include an antimicrobial metal, such as copper, silver, or gold. In several exemplary embodiments, the metal may be elemental silver, powdered silver, silver ions ($Ag^+$), or a silver bearing material like silver oxide (AgO). The hydrophilic layer may thus be an antimicrobial (AM) layer. In this way the colonization-inhibiting properties of the hydrophilic surface can be reinforced by anti-microbial properties.

It may be desirable for the metal to be released over time, while the medical device is in use. In one embodiment, therefore, a silver-bearing time-release material may be a phosphorus-based glass material that dissolves in water at a rate that may be a function of its particular formulation. The glass may also contain trace amounts of other elements, such as calcium oxide (CaO). The rate at which silver is released may further be a function of the rate at which the phosphorus-based glass material dissolves in water. The silver, or the phosphorus-based glass material, or both, may be powdered. The release of silver over time, which is defined as the elution rate and is measured in micrograms/$cm^2$/day, may thus be tailored to the specific needs of the application by specifying the formulation of the phosphorus-based glass material, such as the material described in U.S. Pat. No. 6,143,318. In one embodiment, the silver bearing material may be made up of about 5-10% by weight, e.g. about 7.5% phosphorus-based glass by weight. Such a material is available from Giltech Limited, 12 North Harbour Industrial Estate, Ayr, Scotland, Great Britain KA8 8BN. In one embodiment, the elution rate should be up to about 0.01 micrograms/$cm^2$/day. In another embodiment, the elution rate may be between about 0.01 and 1.0 micrograms/$cm^2$/day. In another embodiment, the elution rate may be about 0.4 micrograms/$cm^2$/day.

In other embodiments, bioactive pharmaceutical agents such as a bronchodilator, an anti-inflammatory agent, or a local anesthetic may be substantially dispersed in a phosphorus-based glass material within a hydrophilic layer. Such bioactive pharmaceutical agents may be delivered to and absorbed by adjacent tissues in substantially the same manner as silver. Regulation and control of dosage, elution rate, and thickness in substantially the same manner as silver may also provide a beneficial pharmacologic or therapeutic action.

A hydrophilic coating may be applied to the surface of a medical device by, e.g. extruding, molding, dipping, spraying, washing, or painting the hydrophilic coating on the surface. In one embodiment, a medical device may be formed by extruding a wall of hydrophobic material along with one or more layers of an antimicrobial material. In another embodiment, a medical device may be formed by molding a wall of hydrophobic material along with one or more layers of an antimicrobial material. The antimicrobial layer may be formed on an inner or an outer surface of the medical device wall. The antimicrobial layer may be comprised of, e.g. polyurethane, such as a medical grade hydrophilic thermoplastic polyurethane into which has been substantially dispersed a silver bearing phosphorus-based glass material. In one embodiment, the antimicrobial layer may be within a range of about 0.002 mm-2.5 mm in thickness, or about 0.13 mm in thickness. In another embodiment, the antimicrobial layer may be within a range of about 0.002 mm-2.5 mm in thickness. In another embodiment, the antimicrobial layer may be up to about 6.35 mm in thickness. In another embodiment, the hydrophobic polymer, hydrophilic polymer and the antimicrobial compound may be compounded together and extruded to form a cuff wall 24.

The tracheal cuffs of the present techniques may be incorporated into systems that facilitate positive pressure ventilation of a patient, such as a ventilator. Such systems may typically include connective tubing, a gas source, a monitor, and/or a controller. The controller may be a digital controller, a computer, an electromechanical programmable controller, or any other control system.

Typically, endotracheal cuffs are inflated within a patient's trachea such that the intra cuff pressure is approximately 20-25 cm $H_2O$. Endotracheal cuffs utilizing inflation pressures significantly greater 25 cm $H_2O$ may be referred to as high-pressure cuffs, while cuffs that are able to effectively seal the trachea at pressures less than 30 cm $H_2O$ may be considered low-pressure cuffs. In certain embodiments, intra cuff inflation pressures of 10-30 cm $H_2O$ may be used with the tapered cuffs of the present techniques.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. An inflatable balloon cuff comprising:
    a tapered section running along at least 50% of a length of the inflatable balloon cuff comprising:
    a sealing portion, wherein the sealing portion is adapted to form a wrinkle-free sealing band at least 1 millimeter in length against a patient's tracheal wall only when inflated;
    a wrinkled portion, wherein a largest diameter of the wrinkled portion is larger than a tracheal diameter such that the wrinkled portion forms a wrinkled band against a patient's tracheal wall when inflated and wherein the wrinkled band is longer than the wrinkle-free sealing band; and
    a minimal contact portion, wherein a largest diameter of the minimal contact region is less than the tracheal diameter.

2. The balloon cuff of claim 1, wherein the tapered section comprises a substantially constant taper rate along the length of the tapered section.

3. The balloon cuff of claim 1, wherein the wrinkle-free sealing band is between 1-3 millimeters in length.

4. The balloon cuff of claim 1, wherein the wrinkle-free sealing band is between 3-6 millimeters in length.

5. The balloon cuff of claim 1, wherein the balloon cuff comprises polyethylene teraphthalate (PETP), low-density polyethylene (LDPE), polyvinyl chloride (PVC), silicone, neoprene, polyisoprene, polypropylene, or polyurethane (PU).

6. The balloon cuff of claim 1, comprising a tracheal tube associated with the balloon cuff, wherein the tracheal tube passes through a proximal opening and a distal opening of the balloon cuff.

7. The balloon cuff of claim 6, wherein the tracheal tube is operatively connected to a ventilator.

8. The balloon cuff of claim 6, wherein the tracheal tube comprises a distal end adapted to be inserted into a patient's trachea and a proximal end, and wherein a tapered section tapers towards the distal end of the tracheal tube or the proximal end of the tracheal tube.

9. The balloon cuff of claim 6, wherein the tapered section comprises a substantially nonlinear taper rate along at least a portion of the length of the tapered section.

10. The balloon cuff of claim 1, comprising an antimicrobial coating on at least a portion of a balloon wall.

11. The balloon cuff of claim 1, wherein narrowest portion of the tapered section has a balloon wall diameter that is less than 0.60 inches when the balloon cuff is fully inflated.

12. The balloon cuff of claim 1, wherein the tapered section comprises balloon wall diameters between 1.75 inches and 0.15 inches when the balloon cuff is fully inflated.

13. The balloon cuff of claim 1, wherein the tapered section comprises balloon wall thicknesses between 0.5 mils and 3 mils.

14. A method of manufacturing an inflatable balloon cuff comprising:
providing an inflatable balloon cuff having a tapered section comprising:
a sealing portion, wherein the sealing portion is adapted to form a wrinkle-free sealing band at least 1 millimeter in length against a patient's tracheal wall only when inflated;
a wrinkled portion, wherein a largest diameter of the wrinkled portion is larger than a tracheal diameter such that the wrinkled portion forms a wrinkled band against a patient's tracheal wall when inflated and wherein the wrinkled band is longer than the wrinkle-free sealing band; and
a minimal contact portion, wherein a largest diameter of the minimal contact region is less than a tracheal diameter.

15. A method of sealing a patient's trachea comprising:
inflating a balloon cuff comprising a tapered section in the patient's trachea,
wherein at least a portion of the balloon cuff is adapted to form a wrinkle-free sealing band against a patient's tracheal wall only when inflated, wherein the wrinkle-free sealing band is at least 1 millimeter in length;
wherein at least a portion of the balloon cuff is adapted to form a wrinkled portion, wherein a largest diameter of the wrinkled portion is larger than a tracheal diameter such that the wrinkled portion forms a wrinkled band against the patient's tracheal wall when inflated and wherein the wrinkled band is longer than the wrinkle-free sealing band; and
wherein at least a portion of the balloon cuff is adapted to form a minimal contact portion, wherein a largest diameter of the minimal contact region is less than a tracheal diameter.

16. An inflatable balloon cuff comprising:
a tapered section comprising at least a portion of the balloon cuff, wherein at least a portion of a balloon wall in the tapered section are less than 60 microns in thickness and wherein a thickness of the balloon wall is not constant along the tapered section regardless of whether the tapered section is inflated or deflated and wherein at least a portion of the tapered section is adapted to form a wrinkle-free sealing band at least 1 millimeter in length against a patient's tracheal wall only when inflated.

17. The balloon cuff of claim 15, wherein the tapered section comprises a substantially constant taper rate along the length of the tapered section.

18. The balloon cuff of claim 15, wherein the tapered section comprises at least 50% of the length of the cuff.

19. The balloon cuff of claim 15, wherein the balloon cuff comprises polyethylene teraphthalate (PETP), low-density polyethylene (LDPE), polyvinyl chloride (PVC), silicone, neoprene, polyisoprene, or polyurethane (PU).

20. The balloon cuff of claim 15, comprising a tracheal tube associated with the balloon cuff, wherein the tracheal tube passes through a proximal opening and a distal opening of the balloon cuff.

21. The balloon cuff of claim 20, wherein the tracheal tube is operatively connected to a ventilator.

22. The balloon cuff of claim 20, wherein the tracheal tube comprises a distal end adapted to be inserted into a patient's trachea and a proximal end, and wherein the tapered section tapers towards the distal end of the tracheal tube or the proximal end of the tracheal tube.

23. The balloon cuff of claim 16, wherein the tapered section comprises a substantially nonlinear taper rate along at least a portion of the length of the tapered section.

24. The balloon cuff of claim 16, comprising an antimicrobial coating on at least a portion of the balloon wall.

25. The balloon cuff of claim 16, wherein narrowest portion of the tapered section has a balloon wall diameter that is less than 0.60 inches when the balloon cuff is fully inflated.

26. The balloon cuff of claim 16, wherein the tapered section comprises balloon wall diameters between 1.75 inches and 0.15 inches when the balloon cuff is fully inflated.

27. A method of manufacturing an inflatable balloon cuff comprising:
providing an inflatable balloon cuff having a tapered section comprising at least a portion of the balloon cuff, wherein a balloon wall in at least a portion of the tapered section are less than 60 microns in thickness and wherein a thickness of the balloon wall is not constant along the tapered section regardless of whether the tapered section is inflated or deflated and wherein at least a portion of the tapered section is adapted to form a wrinkle-free sealing band at least 1 millimeter in length against a patient's tracheal wall only when inflated.

28. An inflatable balloon cuff comprising:
a proximal opening and a distal opening in a wall of the balloon cuff;
a first tapered section along an imaginary axis connecting the proximal opening and the distal opening of the inflated balloon cuff; and
a second tapered section along the imaginary axis connecting the proximal opening and the distal opening, wherein the second tapered section is disposed distally on the cuff relative to the first tapered section, wherein the first tapered section and the second tapered section taper away from one another, and wherein at least a portion of the first tapered section or the second tapered section is adapted to form a wrinkle-free sealing band at least 1 millimeter in length against a patient's tracheal wall only when inflated and wherein a widest diameter of the first tapered section and the second tapered section is greater than the tracheal diameter.

29. The balloon cuff of claim 28, wherein the first tapered section or the second tapered section comprises a substantially constant taper rate along the length of the first or second tapered section.

30. The balloon cuff of claim 28, wherein the balloon cuff comprises polyethylene teraphthalate (PETP), low-density polyethylene (LDPE), polyvinyl chloride (PVC), silicone, neoprene, polyisoprene, or polyurethane (PU).

31. The balloon cuff of claim 28, comprising a tracheal tube coupled to the balloon cuff, wherein the tracheal tube passes through the proximal and distal openings in the wall of the balloon cuff.

32. The balloon cuff of claim 31, wherein the tracheal tube is operatively connected to a ventilator.

33. The balloon cuff of claim 28, comprising an antimicrobial coating on at least a portion of the balloon cuff.

34. The balloon cuff of claim 28, wherein at least one tapered section comprises balloon wall diameters between 1.75 inches and 0.15 inches when the balloon cuff is fully inflated.

35. The balloon cuff of claim 28, wherein the at least one tapered section comprises a substantially nonlinear taper rate along at least a portion of the length of the tapered section.

36. The balloon cuff of claim 28, wherein the widest diameter portion of the first tapered section is proximate to the widest diameter portion of the second tapered section.

37. The balloon cuff of claim 28, wherein a narrowest diameter portion of the first tapered section is proximate to a narrowest diameter portion of the second tapered section.

38. The inflatable balloon cuff of claim 1, wherein the balloon cuff is adapted to be less than two times the diameter of an average adult trachea at its widest point when fully inflated outside the patient.

39. An inflatable balloon cuff comprising:
a tapered section, wherein at least a portion of the tapered section is adapted to form a wrinkle-free sealing band at least 1 millimeter in length against a patient's tracheal wall only when the balloon cuff is inflated within the trachea;
and wherein at least a portion of the tapered section is adapted to form a wrinkled band against the tracheal wall, wherein the wrinkled band is longer than the wrinkle-free sealing band, when the balloon cuff is inflated within the trachea.

40. The inflatable balloon cuff of claim 39, wherein the wrinkled band comprising wrinkles is disposed distally on the cuff relative to the wrinkle-free sealing band.

41. The inflatable balloon cuff of claim 39, wherein the wrinkled band comprising wrinkles is disposed proximally on the cuff relative to the wrinkle-free sealing band.

42. An inflatable balloon cuff comprising:
a tapered section comprising at least a portion of the balloon cuff, wherein a balloon wall in the tapered portion is greater than 20 microns but less than 60 microns in thickness, and wherein at least a portion of the tapered section is adapted to form a wrinkle-free sealing band at least 1 millimeter in length against a patient's tracheal wall only when inflated and wherein a widest diameter of the inflatable balloon cuff is proximal of a midpoint of the inflatable balloon cuff along an imaginary axis connecting a proximal opening and distal opening of the inflatable balloon cuff.

43. The inflatable balloon cuff of claim 39, wherein a wall thickness at a largest diameter portion of the tapered section is less than a wall thickness at a smallest diameter portion of the tapered section.

44. The inflatable balloon cuff of claim 1, wherein the largest diameter of the wrinkled portion is equal to or less than 1.5 times an average adult tracheal diameter.

45. An inflatable balloon cuff comprising:
a tapered section along at least 50% of the length along an imaginary axis of the inflated balloon cuff connecting a proximal opening and distal opening of the inflatable balloon cuff, the tapered section comprising:
a wrinkled portion, wherein a largest diameter of the wrinkled portion is larger than a tracheal diameter such that the wrinkled portion forms folds against a patient's tracheal wall when inflated;
a sealing portion, wherein the sealing portion is adapted to form a wrinkle-free sealing band at least 1 millimeter in length against a patient's tracheal wall only when inflated; and
a minimal contact portion, wherein a largest diameter of the minimal contact region is less than the tracheal diameter; and
a rounded portion, wherein the rounded portion extends to a proximal shoulder of the inflatable balloon cuff and wherein the rounded portion is proximal to the wrinkled portion and wherein the rounded portion comprises a largest diameter of less than 1.35 inches.

46. An inflatable balloon cuff comprising:
a tapered section along at least 50% of the length along an imaginary axis of the inflated balloon cuff connecting a proximal opening and distal opening of the inflatable balloon cuff, the tapered section comprising:
a wrinkled portion, wherein a largest diameter of the wrinkled portion is larger than a tracheal diameter such that the wrinkled portion forms folds against a patient's tracheal wall when inflated; and
a sealing portion, wherein the sealing portion is adapted to form a wrinkle-free sealing band at least 1 millimeter in length against a patient's tracheal wall only when inflated, and wherein the wrinkle-free sealing band is proximal of a midpoint of the imaginary axis; and
a minimal contact portion, wherein a largest diameter of the minimal contact region is less than the tracheal diameter.

* * * * *